US011403752B2

(12) United States Patent
Leporq et al.

(10) Patent No.: US 11,403,752 B2
(45) Date of Patent: Aug. 2, 2022

(54) METHOD FOR POST-PROCESSING LIVER MRI IMAGES TO OBTAIN A RECONSTRUCTED MAP OF THE INTERNAL MAGNETIC SUSCEPTIBILITY

(71) Applicants: INSTITUT NATIONAL DE LA SANTE ET DE LA RECHERCHE MEDICALE (INSERM), Paris (FR); UNIVERSITÉ PARIS DIDEROT—PARIS 7, Paris (FR); CENTRE NATIONAL DE LA RECHERCHE SCIENTIFIQUE, Paris (FR); ASSISTANCE PUBLIQUE—HOPITAUX DE PARIS, Paris (FR); UNIVERSITE DE VERSAILLES SAINT-QUENTIN-EN-YVELINES, Versailles (FR)

(72) Inventors: Benjamin Leporq, Villeurbanne (FR); Simon Lambert, Villeurbanne (FR); Bernard Van Beers, Paris (FR)

(73) Assignees: INSTITUT NATIONAL DE LA SANTE ET DE LA RECHERCHE MEDICALE (INSERM), Paris (FR); UNIVERSITE PARIS DIDEROT—PARIS 7, Paris (FR); CENTRE NATIONAL DE LA RECHERCHE SCIENTIFIQUE, Paris (FR); ASSISTANCE PUBLIQUE—HOPITAUX DE PARIS, Paris (FR); UNIVERSITE DE VERSAILLES SAINT-QUENTIN-EN-YVELINES, Versailles (FR)

( * ) Notice: Subject to any disclaimer, the term of this patent is extended or adjusted under 35 U.S.C. 154(b) by 737 days.

(21) Appl. No.: 16/332,749

(22) PCT Filed: Sep. 12, 2017

(86) PCT No.: PCT/EP2017/072868
§ 371 (c)(1),
(2) Date: Mar. 12, 2019

(87) PCT Pub. No.: WO2018/050627
PCT Pub. Date: Mar. 22, 2018

(65) Prior Publication Data
US 2021/0287359 A1 Sep. 16, 2021

(30) Foreign Application Priority Data
Sep. 13, 2016 (EP) .................................... 16306161

(51) Int. Cl.
*G06K 9/00* (2022.01)
*G01V 3/08* (2006.01)
(Continued)

(52) U.S. Cl.
CPC .......... *G06T 7/0012* (2013.01); *A61B 5/0033* (2013.01); *A61B 5/4244* (2013.01);
(Continued)

(58) Field of Classification Search
CPC ....................................................... G01V 3/08
(Continued)

(56) References Cited

U.S. PATENT DOCUMENTS

| 10,646,134 B2* | 5/2020 | Leporq | G01R 33/5615 |
| 2012/0141003 A1* | 6/2012 | Wang | G01R 33/5608 |
| | | | 382/131 |

(Continued)

OTHER PUBLICATIONS

De Rochefort et al. "Quantitative susceptibility map reconstruction from MR phase data using bayesian regularization: Validation and application to brain imaging", Magnetic Resonance in Medicine, 2010, p. 194-206, vol. 63, Issue 1, first published 2009.*

(Continued)

Primary Examiner — Seyed H Azarian
(74) Attorney, Agent, or Firm — Nixon & Vanderhye

(57) ABSTRACT

In the field of obesity related disease, identification of patients with nonalcoholic steatohepatitis (NASH) would be useful to counsel them more intensively on diet and lifestyle changes and propose new pharmacological treatments. As a consequence, the inventors worked on a method for post-processing images of a region of interest of the liver for reconstructing a map of the internal magnetic susceptibility by using a Bayesian regularization approach to inverse the internal magnetic field. Such method can be implemented on computer and provides better results than other known methods for obesity related disease. This method may be applied for predicting that a subject is at risk of suffering from such disease, diagnosing a disease, identifying a therapeutic or a biomarker and screening compounds useful as a medicine.

14 Claims, 8 Drawing Sheets

(51) Int. Cl.

| | | |
|---|---|---|
| G06T 7/00 | (2017.01) | |
| A61B 5/00 | (2006.01) | |
| G01R 33/56 | (2006.01) | |
| G01R 33/561 | (2006.01) | |
| G01R 33/565 | (2006.01) | |

(52) U.S. Cl.
CPC .......... *A61B 5/4839* (2013.01); *A61B 5/4872* (2013.01); *A61B 5/7275* (2013.01); *G01R 33/5608* (2013.01); *G01R 33/5615* (2013.01); *G06T 2207/10088* (2013.01); *G06T 2207/30056* (2013.01)

(58) Field of Classification Search
USPC ....... 382/100, 103, 128–133, 155, 164, 168, 382/173, 181, 199, 219, 254, 276, 382/285–291, 305, 312; 324/309, 331, 324/320
See application file for complete search history.

(56) References Cited

U.S. PATENT DOCUMENTS

2015/0309137 A1* 10/2015 Bydder ................. G01R 33/34
324/309
2018/0132787 A1* 5/2018 Leporq ............. G01R 33/5608
2020/0335214 A1* 10/2020 Garteiser ........... G01R 33/4828

OTHER PUBLICATIONS

De Rochefort et al., "Quantitative susceptibility map reconstruction from MR phase data using Bayesian regularization: Validation and application to brain imaging", Magnetic Resonance in Medicine, 2010, pp. 194-206, vol. 63, Issue 1, first published 2009.
Berkin et al., "MRI estimates of brain iron concentration in normal aging using quantitative susceptibility mapping", NeuroImage, 2012, vol. 59, Issue 3, pp. 2625-2635.
Liu et al., "A novel background field removal method for MRI using projection onto dipole fields", NMR In Biomedicine, 2011, pp. 1129-1136, vol. 24, No. 9.
Li et al., "Reducing the object orientation dependence of susceptibility effects in gradient echo MRI through quantitative susceptibility mapping", Magnetic Resonance in Medicine, 2012, pp. 1563-1569, vol. 68, Issue 5.
Leporq et al., "Quantification of the triglyceride fatty acid composition with 3.0 T MRI", NMR In Biomedicine, 2014, pp. 1211-1221, vol. 27, Issue 10.
Dong et al., "Simultaneous Phase Unwrapping and Removal of Chemical Shift (SPURS) Using Graph Cuts Application in Quantitative Susceptibility Mapping", IEEE Transactions on Medical Imaging, 2015, pp. 531-540, vol. 34, No. 2.
Hernando et al., "Magnetic susceptibility as a B0 field strength independent MRI biomarker of liver iron overload", Magnetic Resonance in Medicine, 2013, pp. 648-656, vol. 70, Issue 3.
Liu et al., "Method for B0 off-resonance mapping by non-iterative correction of phase-errors (B0-NICE)", Magnetic Resonance in Medicine, 2015, pp. 1177-1188, vol. 74, Issue 4.
International Search Report and Written Opinion, dated Nov. 24, 2017, from corresponding PCT application No. PCT/EP2017/072868.

\* cited by examiner

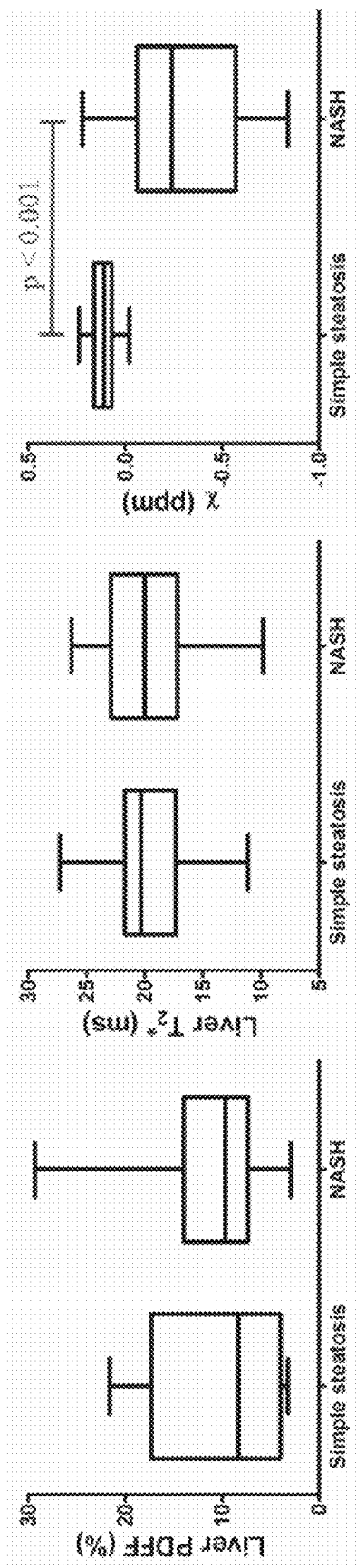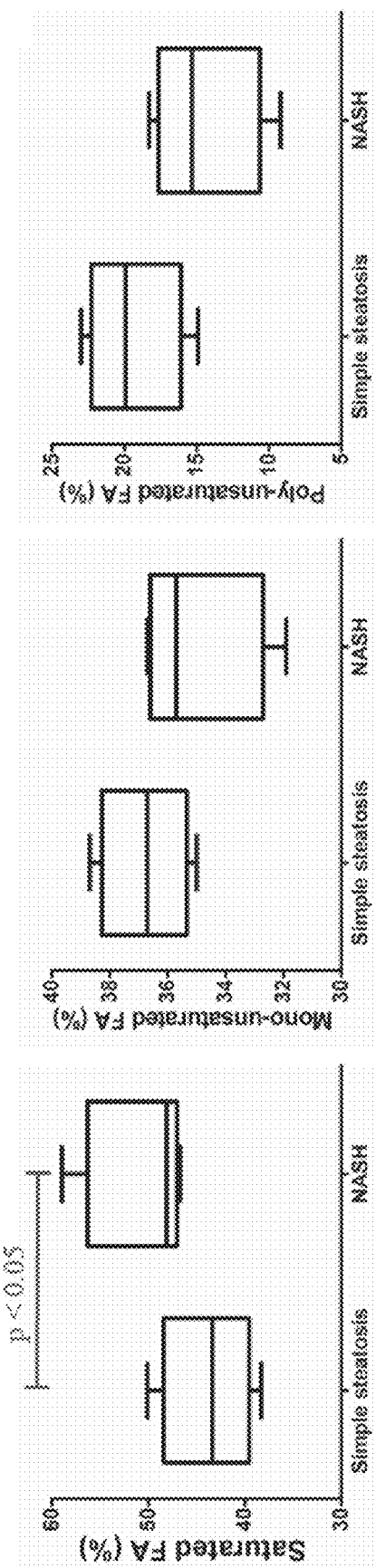
FIG. 20　FIG. 21　FIG. 22　FIG. 23　FIG. 24　FIG. 25

METHOD FOR POST-PROCESSING LIVER MRI IMAGES TO OBTAIN A RECONSTRUCTED MAP OF THE INTERNAL MAGNETIC SUSCEPTIBILITY

TECHNICAL FIELD OF THE INVENTION

The invention is relative to a method for post-processing images of a region of interest of the liver of a subject. The invention concerns a method for predicting that a subject is at risk of suffering from an obesity related disease. The invention also relates to a method for diagnosing an obesity related disease. The invention also concerns a method for identifying a therapeutic target for preventing and/or treating an obesity related disease. The invention also relates to a method for identifying a biomarker, the biomarker being a diagnostic biomarker of an obesity related disease, a prognostic biomarker of an obesity related disease or a predictive biomarker in response to the treatment of an obesity related disease. The invention also concerns a method for screening a compound useful as a medicine, the compound having an effect on a known therapeutical target, for preventing and/or treating an obesity related disease. The invention also relates to the associated computer program products and a computer readable medium.

BACKGROUND OF THE INVENTION

An obesity related disease is a cancer, type 2 diabetes, a heart disease, a liver disease or a non-alcoholic fatty liver disease (NAFLD). Such kinds of diseases concern a high number of people in the world.

There is therefore a need to be able to predict with accuracy the risk for a subject to suffer from this disease.

Nonalcoholic fatty liver disease (NAFLD) and its most severe form, nonalcoholic steatohepatitis (NASH), are associated with high fat diet, high triglyceride levels, obesity, the metabolic syndrome and type II diabetes, and pose an increased risk of cardio vascular disease. NAFLD is an accumulation of fat in the liver that is not a result of excessive consumption of alcohol. 15% to 25% of cases of NAFLD progress and are associated with inflammation and liver damage; this condition is referred to as NASH. NASH is associated with an increased risk of developing liver cirrhosis and subsequence complications, including hepatocellular carcinoma.

Among the previous cited pathologies, in the past decade, an epidemic increase in NAFL) prevalence has been observed. NAFLD is closely associated with the metabolic syndrome, defined by various features including central obesity, diabetes mellitus, raised blood pressure, increased triglyceride levels and decreased high-density lipoprotein-cholesterol. Nowadays, in Western countries, NAFLD is among the most common causes of chronic liver disease with a prevalence ranging between 17 and 46%. NAFLD includes simple steatosis and NASH. Whereas pure steatosis has good prognosis, NASH is associated with poor long-term outcome. About 20% of NASH patients eventually develop cirrhosis or hepatocellular carcinoma, so that NASH has become the fastest growing cause of liver-related morbidity/mortality worldwide.

Despite these severe outcomes, NASH is often overlooked or neglected, which is in part explained by limitations in available diagnostic tools. At histology, NASH is characterized by steatosis, hepatocyte ballooning, inflammatory infiltrates, with or without fibrosis. Currently available non-invasive blood tests or imaging methods only assess liver steatosis and fibrosis. Identification of patients with NASH would be useful to counsel them more intensively on diet and lifestyle changes and propose new pharmacological treatments.

SUMMARY OF THE INVENTION

The invention aims at providing a method which involves less invasive technique and provides the best accuracy in the prediction of the risk for a subject to suffer from an obesity related disease. Notably, there is a specific need for accurate identification of patients with NASH.

To this end, the specification describes a method for post-processing images of a region of interest (ROI) of the liver of a subject to obtain determined parameters, the images being acquired with a magnetic resonance imaging technique, the magnetic resonance imaging technique involving successive echoes of a multiple-gradient echo sequence, each image associating to each pixel of the image the amplitude of the measured signal in the magnetic resonance imaging technique and the phase of the measured signal in the magnetic resonance imaging technique, the method for post-processing comprising at least the step of obtaining the heterogeneous magnetic field in each image by unwrapping the phase of each image, to obtain unwrapped images, extracting the first-order phase from the unwrapped images, calculating the heterogeneous magnetic field based on the extracted first-order phase, the heterogeneous magnetic field being the sum of an internal magnetic field and an external magnetic field. The method for post-processing images comprises a step of separating the internal magnetic field from the external magnetic field in the heterogeneous magnetic field by calculating the external magnetic field by decomposing the heterogeneous magnetic field into a field generated by dipoles outside the region of interest (ROI); and subtracting the calculated external magnetic field from the heterogeneous magnetic field using a projection onto dipole field method, to obtain the internal magnetic field. The method for post-processing images also comprises a step of reconstructing a map of the internal magnetic susceptibility based on the internal magnetic field by using a Bayesian regularization approach to inverse the internal magnetic field, the reconstructed map being a determined parameter.

Thanks to the invention, the method enables to simultaneously quantify, in the liver, hepatic fat content, fatty acid composition, transverse relaxation time and magnetic susceptibility from a single, breathhold acquisition. The magnetic susceptibility is relevant to distinguish between simple steatosis and NASH.

Thus, the method involves less invasive technique and provides the best accuracy in the prediction of the risk for a subject to suffer from an obesity related disease.

It is also to be noted that neuromuscular diseases are commonly characterized by a range of abnormalities affecting skeletal muscle such as muscle wasting, inflammation, fibrosis, micro and macroscopic fatty infiltration. In this context, this method can quantify muscle fatty microinfiltration (by calculating the fat fraction), can detect muscle fatty macroinfiltration, can assess inflammation (by calculating the transversal relaxation time, $T_2^*$) and can assess muscle fibrosis (by calculating the internal magnetic susceptibility, $\chi$).

According to further aspects of the invention which are advantageous but not compulsory, the method for post-processing images might incorporate one or several of the following features, taken in any technically admissible combination:

- Said decomposing of the heterogeneous magnetic field comprises using a projection in Hilbert space and minimizing a distance between the field generated by dipoles outside the region of interest and the heterogeneous magnetic field.
- the distance is pondered by a normal distribution.
- the Bayesian regularization approach comprises a first regularization term taking into account the signal to noise ratio of each images.
- the Bayesian regularization approach comprises a second regularization term taking into account the boundary conditions, the second regularization term depending from an invert mask.
- the Bayesian regularization approach comprises a third regularization term depending from the inverse of the amplitude image gradient.
- the steps of separating and reconstructing both implies a minimization, the minimization being carried out by using a conjugate gradient technique.
- the method for post-processing further comprises the step of determining fat characterization parameters, the fat characterization parameters being determined parameters and the step of determining comprises extracting a real signal over echo time for at least one pixel of the unwrapped images, to obtain at least one extracted real signal, calculating fat characterization parameters by using a fitting technique applied on a model, the model being a function which associates to a plurality of parameters each extracted real signal, the plurality of parameters comprising at least two fat characterization parameters and at least one parameter obtained by a measurement, the fitting technique being a non-linear least-square fitting technique using pseudo-random initial conditions.
- the method for post-processing further comprises the step of determining fat characterization parameters, the fat characterization parameters being determined parameters and the step of determining comprises extracting a real signal over echo time for at least one pixel of the unwrapped images, to obtain at least one extracted real signal and calculating fat characterization parameters by using a fitting technique applied on a model, the model being a function which associates to a plurality of parameters each extracted real signal, the plurality of parameters comprising at least two fat characterization parameters and at least one parameter obtained by a measurement, the fitting technique being a non-linear least-square fitting technique using pseudo-random initial conditions.
- the fat characterization parameters are chosen in the group consisting of the number of double bounds, the number of methylene-interrupted double bounds and the chain length.
- the step of determining further comprises measuring the field inhomogeneity in the magnetic field used in the magnetic resonance imaging technique, and measuring the transversal relaxivity rate or transversal relaxation time, the determined parameter being a measurement of the field inhomogeneity in the magnetic field used in the magnetic resonance imaging technique and the transversal relaxivity rate.
- calculating fat characterization parameters comprises several operations of calculating by using the model in which at least one parameter is fixed.
- the step of determining comprises quantifying the proportion of unsaturated fatty acids and the proportion of saturated fatty acids in the region of interest in the subject based on the calculated fat characterization parameters.
- quantifying the proportion of unsaturated fatty acids and the proportion of saturated fatty acids in the region of interest comprises determining the fatty acid composition based on the calculated fat characterization parameters.

The specification describes a method for predicting that a subject is at risk of suffering from an obesity related disease, the method for predicting at least comprising the step of carrying out the steps of a method for post-processing images of the subject, to obtain determined parameters and the step of predicting that the subject is at risk of suffering from the obesity related disease based on the determined parameters.

The specification also relates to a method for diagnosing an obesity related disease, the method for diagnosing at least comprising the step of carrying out the steps of a method for post-processing images of the subject, to obtain determined parameters and the step of diagnosing the obesity related disease based on the determined parameters.

The specification also concerns a method for identifying a therapeutic target for preventing and/or treating an obesity related disease, the method comprising the step of carrying out the steps of a method for post-processing images of a first subject, to obtain first determined parameters corresponding to the determined parameters for the first subject, the first subject being a subject suffering from the obesity related disease. The method for identifying further comprising the step of carrying out the steps of the method for post-processing images of a second subject, to obtain second determined parameters corresponding to the determined parameters for the second subject, the second subject being a subject not suffering from the obesity related disease, and the step of selecting a therapeutic target based on the comparison of the first and second determined parameters.

The specification also relates to a method for identifying a biomarker, the biomarker being a diagnostic biomarker of an obesity related disease, a prognostic biomarker of an obesity related disease or a predictive biomarker in response to the treatment of an obesity related disease, the method comprising the step of carrying out the steps of a method for post-processing images of a first subject, to obtain first determined parameters, the first determined parameters corresponding to the determined parameters for the first subject, the first subject being a subject suffering from the obesity related disease. The method for identifying further comprising the step of carrying out the steps of the method for post-processing images of a second subject, to obtain second determined parameters corresponding to the determined parameters for the second subject, the second subject being a subject not suffering from the obesity related disease, and the step of selecting a biomarker based on the comparison of the first and second determined parameters.

The specification also concerns a method for screening a compound useful as a medicine, the compound having an effect on a known therapeutic target, for preventing and/or treating an obesity related disease, the method comprising a step of carrying out the steps of a method for post-processing images of a first subject, to obtain first determined parameters, the first determined parameters corresponding to the determined parameters for the first subject, the first subject being a subject suffering from the obesity related disease and having received the compound. The method also comprises a step of carrying out the steps of the method for post-processing images of a second subject, to obtain second determined parameters, the second determined parameters corresponding to the determined parameters for the second subject, the second subject being a subject suffering from the obesity related disease and not having received the compound. The method also comprises a step of selecting a compound based on the comparison of the first and second determined parameters.

The specification also describes a computer program product comprising instructions for carrying out the steps of any method chosen among the previously described method for post-processing, method for predicting, method for diagnosing, method for identifying a therapeutic target, method for identifying a biomarker and the method for screening a compound useful as a medicine when said computer program product is executed on a suitable computer device.

The specification also describes a computer readable medium having encoded thereon a computer program as previously described.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
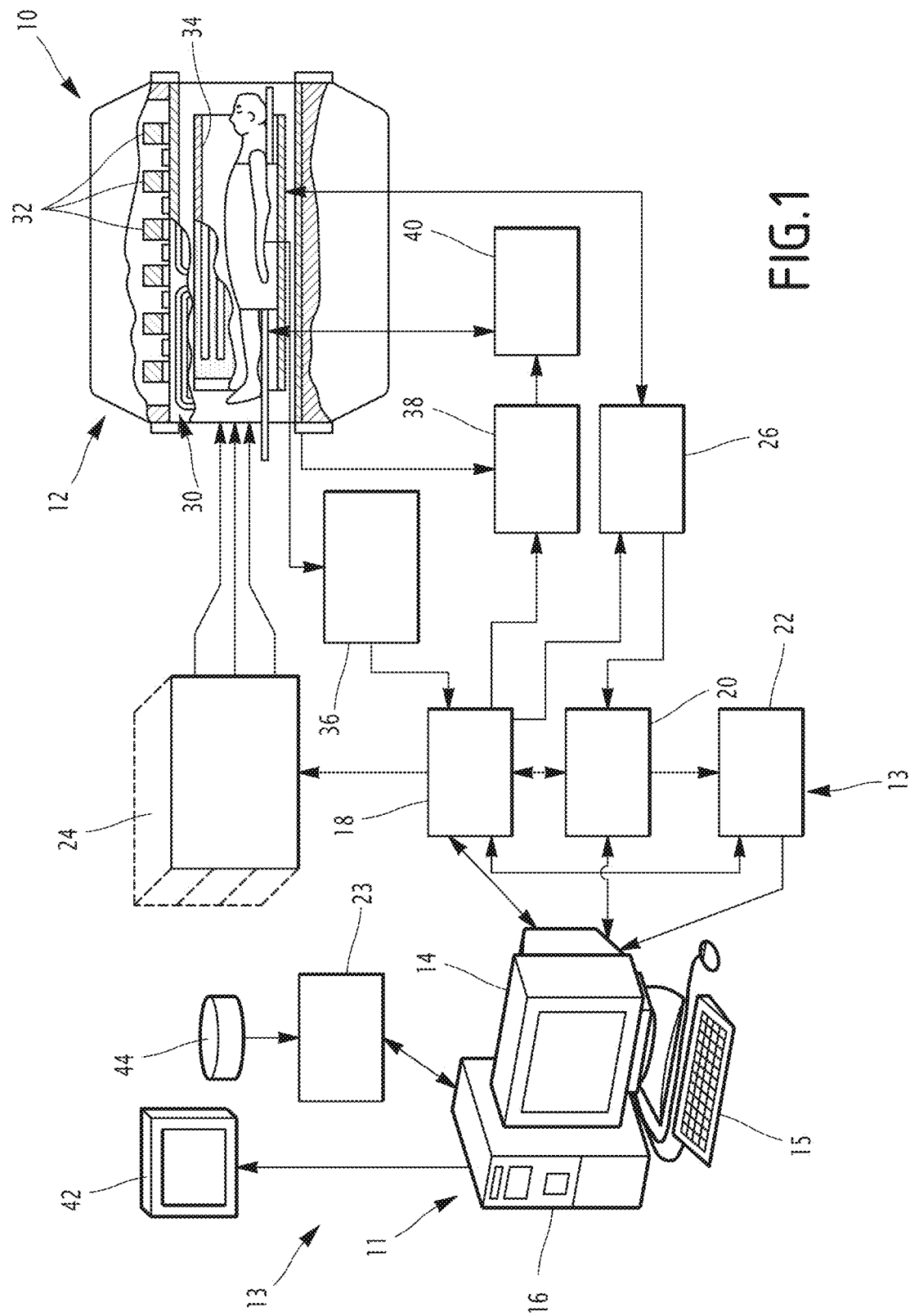
FIG. 1 shows schematically a device for analyzing a region of interest of the liver of a subject.

Description of a Device for Analyzing a Region of Interest of the Liver of a Subject A device 10 for analyzing a region of interest of the liver of a subject is illustrated on FIG. 1.

The device 10 is a device devoted to a clinical use.

According to another embodiment, the device 10 is adapted for a preclinical use.

The region of interest is noted ROI in the remainder of the specification.

The device 10 comprises a calculator 11, a magnetic resonance imaging system 12 and four servers 13.

The calculator 11 is adapted to carry out a method for post-processing images of a region of interest ROI of the liver of a subject to obtain determined parameters.

Notably, the calculator 11 is adapted to receive the obtained images of the region of interest ROI from the magnetic resonance imaging system 12, each image associating to each pixel of the image the amplitude of the measured signal in the magnetic resonance imaging technique and the phase of the measured signal in the magnetic resonance imaging technique.

The calculator 11 is also adapted to obtain the heterogeneous magnetic field in each image.

The calculator 11 is further adapted to unwrap the phase of each image, to obtain unwrapped images.

The calculator 11 is also adapted to calculate the heterogeneous magnetic field based on the extracted first-order phase, the heterogeneous magnetic field being the sum of an internal magnetic field and an external magnetic field.

The calculator 11 is further adapted to separate the internal magnetic field from the external magnetic field in the heterogeneous magnetic field by using a projection onto dipole field method.

The calculator 11 is also adapted to reconstruct a map of the internal magnetic susceptibility based on the internal magnetic field by using a Bayesian regularization approach to inverse the internal magnetic field, the reconstructed map being a determined parameter.

The calculator 11 provides the operator interface which enables scan prescriptions to be entered into the magnetic resonance imaging system 30.

According to the embodiment of FIG. 1, the calculator 11 is such that the interaction between a computer program product and the calculator 11 enables to carry out a method for post-processing images.

The calculator 11 is a computer. In the present case, the calculator 11 is a laptop.

More generally, the calculator 11 is a computer or computing system, or similar electronic computing device adapted to manipulate and/or transform data represented as physical, such as electronic, quantities within the computing system's registers and/or memories into other data similarly represented as physical quantities within the computing system's memories, registers or other such information storage, transmission or display devices.

The calculator 11 comprises a display unit 14, a keyboard 15 and a processor 16.

The processor 16 comprises a data-processing unit, memories and a reader. The reader is adapted to read a computer readable medium.

The computer program product comprises a computer readable medium.

The computer readable medium is a medium that can be read by the reader of the processor. The computer readable medium is a medium suitable for storing electronic instructions, and capable of being coupled to a computer system bus.

Such computer readable storage medium is, for instance, a disk, a floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

A computer program is stored in the computer readable storage medium. The computer program comprises one or more stored sequence of program instructions.

The computer program is loadable into the data-processing unit and adapted to cause execution of the method for post-processing images when the computer program is run by the data-processing unit.

The calculator 11 is coupled to the four servers 13

The four servers are a pulse sequence server 18, a data acquisition server 20, a data processing server 22 and a data store server 23.

According to the example of FIG. 1, the data store server 23 is performed by the processor 16 and associated disc drive interface circuitry.

The remaining three servers 18, 20 and 22 are performed by separate processors mounted in a single enclosure and interconnected using a 64-bit backplane bus. The pulse sequence server 18 employs a commercially available microprocessor and a commercially available quad communication controller. The data acquisition server 20 and data processing server 22 both employ the same commercially available microprocessor and the data processing server 22 further includes one or more array processors based on commercially available parallel vector processors.

The calculator 11 and each processor for the servers 18, 20 and 22 are connected to a serial communications network. This serial network conveys data that is downloaded to the servers 18, 20 and 22 from the calculator 11. The network conveys tag data that is communicated between the servers 18, 20, 22 and 23 and between the calculator 11. In addition, a high speed data link is provided between the data processing server 22 and the calculator 1A in order to convey image data to the data store server 23.

The pulse sequence server 18 functions in response to program elements downloaded from the calculator 11 to operate a gradient system 24 and an RF system 26. Gradient waveforms necessary to perform the prescribed scan are produced and applied to the gradient system 24 which excites gradient coils in an assembly 30 to produce the magnetic field gradients $G_x$, $G_y$ and $G_z$ used for position encoding nuclear magnetic resonance NMR signals. NMR is a physical property according to which the nuclei of atoms absorb and re-emit electromagnetic energy at a specific resonance frequency in the presence of a magnetic field.

The gradient coil assembly 30 forms part of a magnet assembly which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal.

The magnitude of the received NMR signal may thus be determined at any sampled point by the square root of the sum of the squares of the I and Q components:

$$M=\sqrt{I^2+Q^2}$$

and the phase of the received NMR signal may also be determined by the following equation:

$$\Phi = \tan^{-1}\left(\frac{Q}{I}\right)$$

The pulse sequence server 18 also optionally receives patient data from a physiological acquisition controller 36. The controller 36 receives signals from a number of different sensors connected to the subject, such as electroencephalogram (ECG) signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the subject and the magnet system. It is also through the scan room interface circuit 38 that a subject positioning system 40 receives commands to move the subject to desired positions during the scan.

It should be apparent that the pulse sequence server 18 performs real-time control of magnetic resonance imaging system elements during a scan. As a result, the hardware elements of the pulse sequence server 18 are operated with program instructions that are executed in a timely manner by run-time programs. The description components for a scan prescription are downloaded from the calculator 11 in the form of objects. The pulse sequence server 18 contains programs which receive these objects and converts them to objects that are employed by the run-time programs.

The digitized NMR signal samples produced by the RF system 26 are received by the data acquisition server 20. The data acquisition server 20 operates in response to description components downloaded from the calculator 11 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with description components downloaded from the calculator 11. Such processing may include Fourier transformation of raw k-space NMR data to produce two or three-dimensional images.

Images reconstructed by the data processing server 22 are conveyed back to the calculator 11 where they are stored. Real-time images are stored in a data base memory cache (not shown) from which they may be output to operator display 14 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the calculator 11.

The magnetic resonance imaging system 12 is adapted to image the region of interest ROI in the liver of the subject by using a magnetic resonance imaging technique, the magnetic resonance imaging technique involving successive echoes of a multiple-gradient echo sequence, to obtain images.

In the case of a preclinical use, the magnetic resonance imaging system 12 is further adapted to apply a magnetic field whose magnetic field value comprised between 1.0 T and 15.2 T.

In case of a clinical use, the magnetic resonance imaging system 12 is further adapted to apply a magnetic field whose magnetic field value comprised between 1.0 T and 7.0 T.

According to a specific embodiment, the magnetic resonance imaging system 12 is adapted to apply a magnetic field whose magnetic field value comprised between 1.5 T and 3.0 T.

Operation of the Device 10

Figure 2:
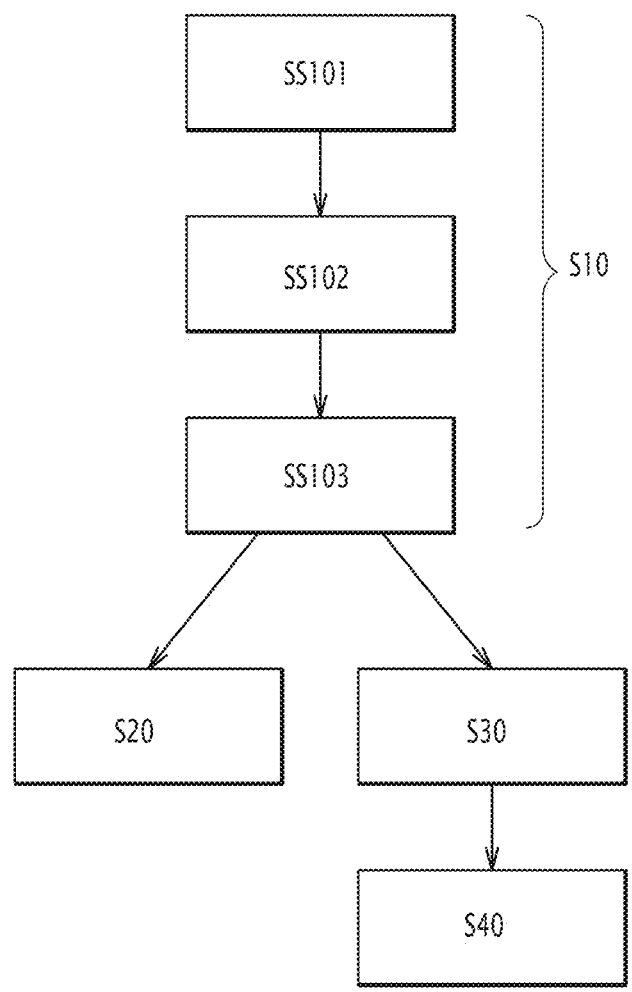
FIG. 2 shows an example of a flowchart illustrating an example of carrying out a method for post-processing images of the region of interest, the method for post-processing comprising a plurality of steps.

Operation of the device 10 is now described by illustrating an example of carrying out the method for post-processing images as illustrated by the flowchart of FIG. 2.

The images post-processed in the method for post-processing images are images of the region of interest ROI of the liver of a subject.

The subject is usually human beings.

In the images/maps of FIGS. 3 to 19 and in the experience described in reference with FIGS. 20 to 28, the subjects are human beings.

The images are acquired with a magnetic resonance imaging technique.

The magnetic resonance imaging technique involving successive echoes of a multiple-gradient echo sequence.

According to the specific embodiment described, the multiple-gradient echo sequence is a spoiled gradient echo sequence.

In addition, the magnetic resonance imaging technique is carried out by a clinical system operating at magnetic field with a magnitude of 3.0 Tesla (T).

Each image associates to each pixel of the image the amplitude of the measured signal in the magnetic resonance imaging technique and the phase of the measured signal in the magnetic resonance imaging technique.

Figure 3:
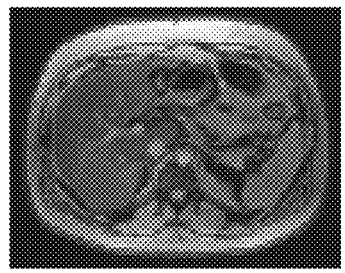
FIGS. 3 to 19 illustrate maps or images obtained at different steps of the method for post-processing of FIG. 2, and FIGS. 20 to 28 illustrate the results obtained by an example of experiment corresponding to the carrying out of the method for post-processing.
Figure 4:
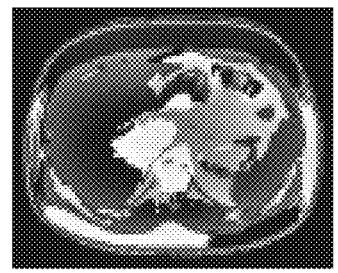
Figure 5:
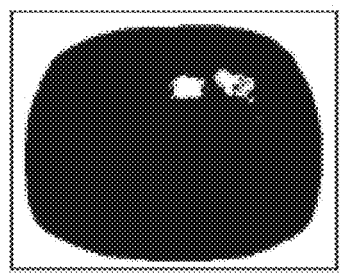
Figure 6:
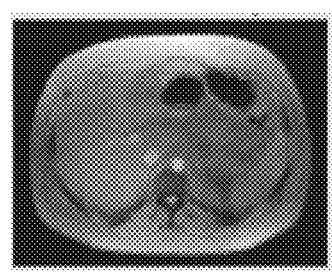
Figure 7:
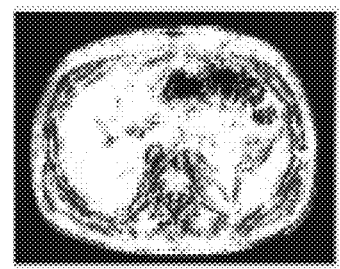

In other words, for each image, it can be defined a magnitude map and a phase map. FIG. 3 is an example of a magnitude map while FIG. 4 is an example of a phase map.

The method for post-processing images enables to obtain determined parameters which are detailed below.

The method for post-processing images comprises a step of obtaining S10 the heterogeneous magnetic field, a step of determining S20, a step of separating S30 and a step of reconstructing S40.

On the Step of Obtaining S10

At the step of obtaining S10, the heterogeneous magnetic field is obtained in each image.

In the example of FIG. 2, the step of obtaining S10 comprises a first substep of unwrapping SS101, a second substep of extracting SS102 and a third substep of calculating SS103.

At the first substep of unwrapping SS101, the phase of each image is unwrapped, to obtain unwrapped images.

For instance, at this first substep SS101, a two-cluster segmentation mask is built from the magnitude images to suppress background and air cavities with a k-means approach and is applied on the phase images.

Then, the multiple echo phase images are unwrapped by adding multiples of $\pm 2\pi$ when absolute jumps between consecutive elements of the array are greater than or equal to a jump tolerance of $\pi$ radians.

At the second substep of extracting SS102, the first-order phase is extracted from the unwrapped images.

From the unwrapped phase images, the zero-order phase (linked to radiofrequency penetration and eddy current effect) and the first-order phase (linked to local heterogeneities in the magnetic field) are extracted pixel-by-pixel.

This procedure is achieved with a weighted linear least-square fit accounting for the phase to noise ratio difference occurring with the echo time $T_E$ and using the spoiled gradient echo sequence model for the MR signal phase $\varphi(T_E)$:

$$\varphi(T_E) = \varphi_0 + \varphi_1 T_E$$

where:

$\varphi_0$ accounts for the zero order phase (in rad), and $\varphi_1$ for the first order phase (in rad·s$^{-1}$).

At the third substep of calculating SS103, the heterogeneous magnetic field is based on the extracted first-order phase.

The heterogeneous magnetic field $B_0$ is deduced using $B_0 = \varphi_1/2\pi$.

Figure 9:
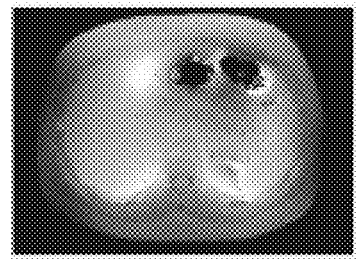
Figure 10:
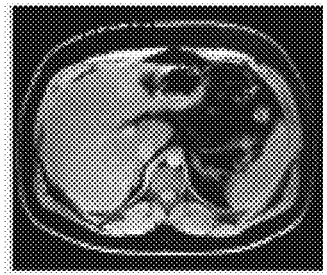
Figure 11:
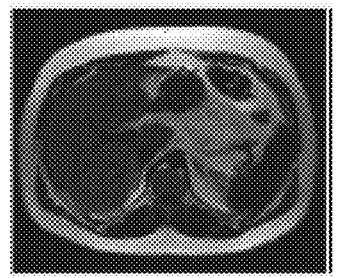
Figure 12:
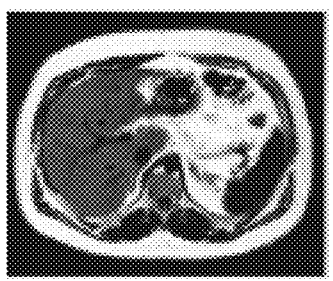
Figure 13:
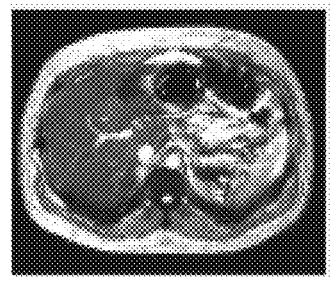
Figure 14:
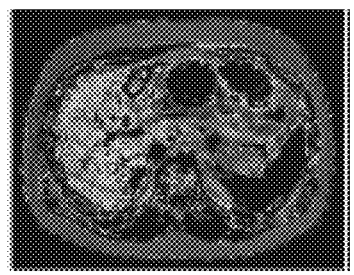
Figure 15:
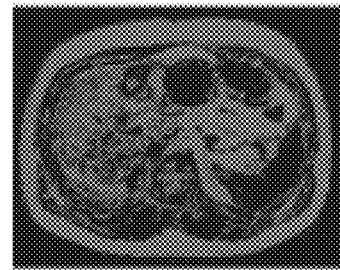
Figure 16:
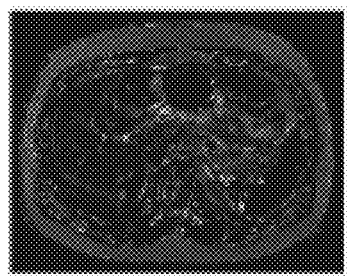

FIG. 9 illustrates an example of a map of the heterogeneous magnetic field $B_0$ in the ROI of a subject.

On the Step of Determining S20

At the step of determining S20, fat characterization parameters are obtained. The fat characterization parameters are determined parameters obtained by the method for post-processing.

As a specific example, the step of determining S20 comprises a substep of correcting, a substep of extracting, a substep of calculating and a substep of quantifying.

At the substep of correcting, the phase of each image is corrected.

For instance, by using the results of the step of obtaining S10, the zero-order phase $\varphi_0$ and the first-order phase $\varphi_1$ are obtained.

Obtaining the zero-order phase $\varphi_0$ and the first-order phase $\varphi_1$ enables to correct multiple echoes phase images for zero-order and first-order phase. Then, real part images are generated from the native magnitude images and the corrected phase images.

At the end of the correcting substep, corrected real images are obtained.

Optionally, at the correcting substep, phase images for zero (time independent) and first order (time-dependent) dephasings are also corrected.

Alternatively, the step of determining S20 comprises a substep of providing corrected real images to be post-processed.

At the substep of extracting, a real signal over echo time $T_E$ for at least one pixel of the unwrapped images is extracted.

Figure 8:
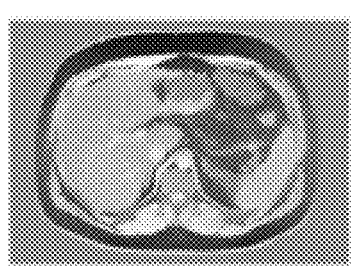

An example of a map corresponding to the real signal is illustrated by FIG. 8.

According to the specific embodiment described, from multiple echo unwrapped real images, a real signal over echo time $S(T_E)$ is extracted pixel by pixel.

At the end of the extracting substep, for each pixel, the real signal over echo time $S(T_E)$ is known.

At the substep of calculating, fat characterization parameters are calculated by using a fitting technique applied on a model.

The model is a model for the real gradient echo signal at time $T_E$ from a pixel containing water and fat with an unknown number of spectral components.

In other words, such model is a function which associates to a plurality of parameters each extracted real signal.

This means that the model is fitted to the extracted real signal in order to derive a plurality of parameters. The plurality of parameters comprises at least two fat characterization parameters.

According to a specific embodiment, the fat characterization parameters are chosen in the group consisting of the number of double bounds ndb, the number of methylene-interrupted double bounds nmidb and the chain length CL.

The model is based on eight separate fat resonances.

The calculating substep comprises several operations of calculating by using the model in which at least one parameter is fixed.

Usually, the fixed parameter(s) differ from one operation to another.

In other words, a stepwise fitting approach is proposed to reduce and keep a constant degree of freedom v.

More precisely, the calculating substep comprises three operations of calculating in the illustrated example.

During the first operation of calculating, separation of fat and water proton densities ($PD_f$ and $PD_w$) is performed with a 3-parameter bi-exponential model of the real part of the signal ($S_{real}$) integrating the modeling of eight fat resonances.

Equation of $S_{real}$ over $T_E$ at steady state conditions with $T_1$ contribution neglected and magnetic inhomogeneities corrected is:

$$S_{real}(TE) = Re\left(\left(PD_w + PD_f \times \sum_{k=1}^{8} C_k e^{2\pi i f_k TE}\right) \times e^{-\frac{TE}{T_2^*}}\right)$$

where:
- $S_{real}(T_E)$ is the real part of signal according to echo time;
- $Re(x)$ designates the real part of x;
- $T_2^*$ is the transversal decay or transverse relaxation time;
- $C_k$ are coefficients equal to the ratio of the fat resonance k signal over the total fat signal, and
- $f_k$ corresponds to the frequency shift between water and each fat resonance k.

From this first operation, the proton density fat fraction (PDFF) is calculated as $PDFF=[PD_f/(PD_f+PD_w)]\times 100$.

During the second operation, the fat spectrum model is modified as follows: the fat components are expressed according to their number of protons and to ndb, nmidb and CL.

The equation of $S_{real}$ over echo time at steady state conditions with $T_1$ contribution neglected and $B_0$ heterogeneity corrected can be expressed as follows:

$$S_{real}(TE) = Re\left(\left(w \times n_{water} + f \times \sum_{k=1}^{8} n_k(ndb, CL, nmidb)e^{2\pi i f_k TE}\right) \times e^{-\frac{TE}{T_2^*}}\right)$$

Where
- w and f represent respectively the number of water and the number of triglycerides molecules,
- $n_k$ (ndb, CL, nmidb) the number of protons in the fat spectrum component k according to ndb, CL and nmidb,
- $f_k$ the frequency shift between water and each fat spectrum component k, and
- $n_{water}$ the number of proton in a water molecule.

During the second operation, CL and nmidb are expressed according to ndb using the two heuristic approximations such as:

$$CL=16.8+0.25\times ndb,$$

and $$nmidb=0.093\times ndb^2.$$

In addition, $T_2^*$ value was used from the previous step. Thus, the fitted parameters are w, f and ndb.

During the third operation, the fitting procedure is reiterated to fit w, f and nmidb. The $T_2^*$-value is obtained from the first sub-step and the ndb-value from the second step. No fitting procedure is conducted to extract CL because this parameter does not give additional information about fatty acid composition saturation.

For each calculation operation, the fitting technique is performed with a non-linear least-square fitting technique using pseudo-random initial conditions.

As an example, the parameters are derived by using a non-linear least-square fit using the multi-start Levenberg-Marquardt algorithm.

In mathematics and computing, the Levenberg-Marquardt algorithm (LMA), also known as the damped least-squares method, is used to solve non-linear least squares problems. These minimization problems arise especially in least squares curve fitting.

The LMA interpolates between the Gauss-Newton algorithm (GNA) and the method of gradient descent. The LMA is more robust than the GNA, which means that in many cases it finds a solution even if it starts very far off the final minimum. For well-behaved functions and reasonable starting parameters, the LMA tends to be a bit slower than the GNA. LMA can also be viewed as Gauss-Newton using a trust region approach.

The LMA is a very popular curve-fitting algorithm used in many software applications for solving generic curve-fitting problems. However, as for many fitting algorithms, the LMA finds only a local minimum, which is not necessarily the global minimum.

A multi-start technique or the use of pseudo-random initial conditions corresponds to the use of a grid of pseudo-random initial conditions. This enables to improve the robustness of optimization and to avoid multiple local minima problem.

In other words, the fitting technique is carried out a certain number of times, each time corresponding to different initial conditions.

For instance, the number of times is superior or equal to five, preferably superior or equal to ten, more preferably superior or equal to twenty.

According to a specific example, the number of times is equal to fifty. This enables to improve the robustness and reliability of optimization, but also to avoid multiple local minima problem.

At the end of the calculating substep, the fat characterization parameters are obtained.

At the substep of quantifying, the proportion of unsaturated fatty acids and the proportion of saturated fatty acids in the region of interest ROI of the subject are obtained based on the calculated fat characterization parameters.

Preferably, at the substep of quantifying, the proportions of saturated, monounsaturated and polyunsaturated fatty acids in the region of interest ROI in the subject are quantified based on the calculated fat characterization parameters.

As an example, the quantifying substep comprises determining the fatty acid composition based on the calculated fat characterization parameters.

For determining the fatty acid composition, it is proposed to use the following relations:

$$F_{UFA} = \frac{ndb - nmidb}{3} \quad F_{PUFA} = \frac{nmidb}{3}$$

Where:

$F_{UFA}$ is the unsaturated fatty acid fraction in %, and
$F_{PUFA}$ is the polyunsaturated fatty acid fraction in %.

Optionally, determining the fatty acid composition also comprises deducing the monounsaturated fatty acid fraction, which is generally labeled $F_{MUFA}$. For this, the following equation may be used:

$$F_{MUFA} = F_{UFA} - F_{PUFA}$$

Optionally, determining the fatty acid composition also comprises calculating the saturated fatty acid fraction, which is generally labeled $F_{SFA}$. For this, the following equation may be used:

$$F_{SFA} = 100 - F_{UFA}$$

In summary, the step of determining S20 enables to achieve fat water separation and to obtain fatty acid composition. For this, a specific phase correction algorithm is used to unwrap and correct the native phase images for zero-order phase and first-order phase and rebuild the $B_0$-demodulated real part images. Then, a model of a fat $^1$H MR spectrum integrating eight components is used to derive the number of double bonds ndb, the number of methylene-interrupted double bonds nmidb and $T_2^*$. The fractions of saturated, mono-unsaturated and polyunsaturated fatty acids are calculated from ndb and nmidb.

Carrying out the step of determining S20 provides fat and water only images as well as several parametric maps, of $T_2^*$, field inhomogeneity, fat fraction and saturated, mono-unsaturated, polyunsaturated fatty acid fractions.

The parametric maps are notably illustrated by FIGS. 10 to 16. The map of FIG. 10 corresponds to the water only map; the map of FIG. 11 corresponds to the fat only map; the map of FIG. 12 corresponds to the fat fraction (FF) map; the map of FIG. 13 corresponds to the transverse relaxation time $T_2^*$ map; the map of FIG. 14 corresponds to the SFA map; the map of FIG. 15 corresponds to the MUFA map and the map of FIG. 16 corresponds to the PUFA map.

At the end of step of determining S20, fat characterization parameters are obtained.

As explained before, the fat characterization parameters may be the fractions of saturated, mono-unsaturated and polyunsaturated fatty acids.

On the Step of Separating S30

This heterogeneous magnetic field $B_0$ is the sum of an internal magnetic field $B_{int}$ and an external magnetic field $B_{ext}$.

At the step of separating S30, the internal magnetic field is separated from the external magnetic field in the heterogeneous magnetic field $B_0$.

The internal field is linked to the internal susceptibility $\chi_{int}$ while the external field is linked to external field heterogeneities caused by shims, $B_1$ inhomogeneity or air-tissue interfaces.

it is necessary to separate the internal field in the ROI from the external field. This external field arises from various sources, including imperfect shimming and magnetic susceptibility sources outside the ROI.

The step of separating S30 provides a projection onto dipole fields method of projecting the heterogeneous field $B_0$ measured in the ROI onto the subspace spanned by external unit dipole fields. The heterogeneous field $B_0$ measured in the ROI and all the external unit dipole fields may be used.

The step of separating S30 is provided for removing external field from the ROI. The step of separating S30 includes calculating the external field by decomposing the field measured inside the region of interest ROI into a field generated by dipoles outside the region of interest ROI and subtracting the calculated external field from the heterogeneous field $B_0$. This enables to obtain the magnetic field $B_{int}$.

According to an embodiment, the decomposing may further include use of a projection in Hilbert space.

The projection onto dipole fields method relies on the fact that the inner product of the field of an external dipole outside the ROI and the field of an internal dipole inside the ROI is almost zero in the ROI, except for internal dipoles near the boundary. This observation forms the foundation for the PDF method to differentiate the internal and external fields.

More precisely, according to the dipole equation, the strength of a dipole field decays on the order of $r^3$, where r is the distance to the dipole, so that the impact of the dipole is strong within its immediate vicinity and diminishes rapidly. Hence, if an internal and an external dipole are far away in space, their spatial overlap, as measured by the normalized inner product, is very small. The separation between internal and external fields may be fundamentally explained by the Maxwell equation, which states that the field generated by the external dipoles is a harmonic function inside the ROI, but the field generated by the internal dipoles is nonharmonic. Therefore, the external and internal fields may be separable in an ideal harmonic function space, what the projection onto dipole fields method guarantees.

Some elements explaining the projection onto dipole fields method are given below.

For the ROI, the internal field $B_{int}$ is defined as the magnetic field generated by the susceptibility distribution $\chi_{int}$ inside an ROI M, and the external field $B_{ext}$ is defined as the magnetic field generated by the susceptibility distribution $\chi_{ext}$ in the region M, which is outside the ROI and inside a sufficiently large field of view (FOV) of the magnetic resonance imaging system 12. The external field $B_{ext}$ extends into the ROI, just as the internal field $B_{int}$ extends outside the ROI. For human MRI, tissue susceptibility satisfies $|\chi| \ll 1$, making the magnetic fields generated by human tissue susceptibility variation orders of magnitudes smaller than the main field. Taking this into account, the total magnetic field is written as the following equation:

$$B_0 = B_{int} + B_{ext} = d \otimes |\chi_{int} + \chi_{ext}|$$

where:

⊗ denotes convolution, and d is the unit dipole field, which is the magnetic field created by a unit dipole at the origin with the Lorentz sphere correction.

In an embodiment, the step of separating comprises projecting the total heterogeneous field measured in the ROI onto the subspace spanned by the external unit dipole fields. The total heterogeneous field measured in the ROI may be used. All the external unit dipole fields may be used. This is related to the projection theorem in Hilbert space which is briefly review below.

Let T be an inner product space spanned by all unit dipole responses $\{d_r | r \in M \cup \overline{M}\}$, where $d_r$ denotes the magnetic field induced by a unit dipole located at r. Hence, the heterogeneous field $B_0 \in T$. The inner product between any $B_1, B_2 \in T$ is defined as the sum of element-wise multiplication between $B_1$ and $B_2$ inside the ROI only. Following the previous equation, the external field component $B_{ext}$ is formed of basis functions $\{d_{rext} | r_{ext} \in \overline{M}\}$, which represent fields created by external unit dipoles. The subspace spanned by all the external unit dipole fields is then denoted as EXT. Similarly, the basis functions of the internal field component $B_{int}$ are $\{d_{rint} | r_{int} \in M\}$ and the subspace spanned by all the internal unit dipole fields is denoted as INT. According to the projection theorem, $\mathrm{argmin}_{B \in EXT} \|B - B_{ext}\|_2$ has a unique value $B^*_B$, and $B - B^*_B$ is orthogonal to EXT; if INT is orthogonal to INT, $B - B_{ext} = B_{int}$ is orthogonal to EXT, and so $B^*_B$ obtained by the minimization is exactly $B_{ext}$, the true external field. In other words, the step of separating S30 estimates the external field as:

$$\mathop{\mathrm{argmin}}_{\chi^{B} \in \overline{M}} \|B_0 - d \otimes \chi_{ext}\|_2$$

This observation relies on the orthogonality assumption which requires that, for each given internal unit dipole field, its inner product with any possible external unit dipole field is zero.

In an embodiment, the computation of the heterogeneous field $B_0$ from MR phase data is based on phase data from multiple echo data followed by a magnitude image-guided unwrapping algorithm. To correct for a large external field from potentially poor shimming, zeroth and first-order spherical harmonic terms in the field expansion are estimated and removed from the measured heterogeneous field $B_0$ using a weighted least-square minimization. The corrected heterogeneous field $B_0$ was then used in all the following external removal methods.

The spatial variations of noise in the MR field maps by adding a weight to the latest equation to normalize the noise to a normal distribution N(0,1). The weight w was derived from magnitude images across multiple echoes. The resulting minimization becomes:

$$\chi_B *= \mathop{\mathrm{argmin}}_{\chi^B} \|w(B_0 - d \otimes \chi_B)\|_2$$

where the norm $\|\cdot\|_2$ in previous equation is again calculated only over the ROI, which may be defined using image segmentation, and the dot symbol indicates point-wise multiplication between vectors.

We let N be the number of voxels in the MR image dataset, and expressed the measured heterogeneous field f and the total susceptibility distribution $\chi$ as N×1 column vectors. Let I be an N×N identity matrix and M an N×N diagonal matrix, where the diagonal elements are equal to unity when they correspond to voxels inside the ROI and are equal to zero otherwise. Then, the external susceptibility was written as $\chi_{ext} = (I-M)\chi$. D denotes an N×N matrix representing the convolution with the unit dipole field d, and W denotes an N×N diagonal matrix formed by placing the weighting w on the diagonal. With this notation, the minimizer in previous equation was found by solving:

$$MWD(I-M)\chi = MWf$$

To simply the storing of the calculation, a conjugate gradient algorithm was used in which the convolution is efficiently calculated in the Fourier domain.

The conjugate gradient method is an iterative algorithm providing the numerical solution of sparse linear equation systems whose matrix is symmetric and positive definite.

The forward system on the left-hand side of MWD(I−M)$\chi$=MWf was made positive semi-definite by applying the Hermitian conjugate of the matrix A=MWD(I−M) to both sides. This results in the equation $A^H A\chi = A^H \beta$ where $\beta$=MWf.

The conjugate gradient algorithm iteration is stopped when the norm of the residual is smaller than 50% of the expected noise level $\|A^H Mu\|_2$, where u is a column vector containing ones. Once $\chi^*$ had been estimated, the external field is calculated as $B_B^* = D\chi_{int}^* = D(I-M)\chi^*$ and is subtracted from the measured heterogeneous field $B_0$ to estimate the internal field $B_{int}$.

Figure 17:
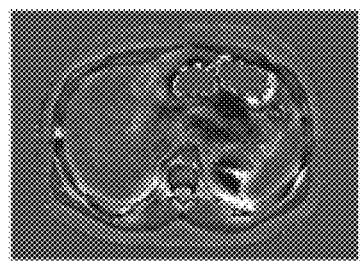
Figure 18:
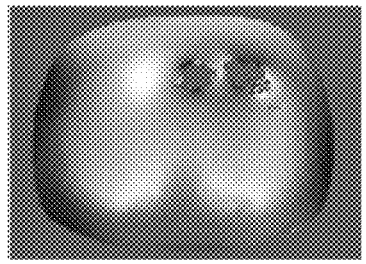

At the end of the step of separating S30, the external field $B_{ext}$ and the internal field $B_{int}$ are known as respectively illustrated by the map of FIG. 18 and FIG. 17.

On the Step of Reconstructing S40

At the step of reconstructing S40, a map of the internal magnetic susceptibility is reconstructed.

Figure 19:
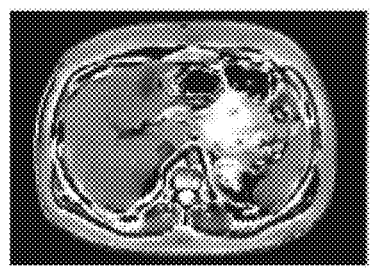

An example of such map is illustrated by FIG. 19.

Such step of reconstructing S40 is achieved based on the internal magnetic field $B_{int}$ by using a Bayesian regularization approach to inverse the internal magnetic field $B_{int}$.

The reconstructed map is a determined parameter for the method for post-processing.

From the integration of the Maxwell magnetostatic equations, the internal field $B_{int}$ generated by a nucleus (assumed to be in a small Lorentzian sphere) can be expressed as the convolution product between an arbitrary susceptibility distribution $\chi_{int}$ and the field generated by the unit dipole d as:

$$B_{int}(\vec{r}) = B_{static} \int_r \frac{3\cos^2(\theta_r) - 1}{4\pi \|\vec{r}\|^3} \chi_{int}(\vec{r}) d^3 r = B_{static}(d \otimes \chi_{int})(\vec{r})$$

Where:

$\theta_{rr'}$ is the angle from the static magnetic field direction, r is the vector position, and $B_{static}$ the magnetic static field intensity.

In the Fourier domain, the non-local expression given by the previous equation becomes a pointwise frequency product:

$$F(B_{int})(\vec{k}) = B_{static} \times F(\chi_{int})(\vec{k}) \times \left(\frac{1}{3} - \frac{k_z^2}{k^2}\right) = F(\chi_{int})(\vec{k}) \times B_{static} \times F(d)(\vec{k})$$

Where:

F corresponds to the Fourier transform, $d(\vec{k})$ is the dipole kernel in k-space, and k is the reciprocal space vector ($k = (k_x^2, k_y^2, k_z^2)^{1/2}$).

This equation can be rewritten in matrix vector form:

$$\widehat{B_{int}} = C \cdot \widehat{\chi_{int}}$$

Where:

C is a sparse Toeplitz matrix representing the convolution kernel $B_0 \times F(d(\vec{k}))$ and $\widehat{\chi_{int}}$ is the susceptibility distribution expressed as a column vector.

At the magic angle (54.7°), $k^2=3k_z^2$ and the dipole response function includes values equal or near to zero. Given that in k-space, this leads to noise amplification and streaking artefacts, C cannot be directly inverted. To overcome this ill-posed problem, a Bayesian regularization is performed by adding regularization terms penalizing the edges in the estimated susceptibility distribution and including boundary conditions.

In other words, a dipole inversion is varied out by using a single orientation Bayesian regularization including spatial priors derived from magnitude images for boundary conditions, error and smoothness weighting. The magnitude images for boundary conditions, error and smoothness weighting are respectively illustrated by FIGS. 5 to 7.

A Bayesian regularization is a Tikhonov-like regularization.

In the first regularization term, the invert mask allows a minimization of borders and therefore imposes the boundary condition.

When referring to "boundary conditions" in the present specification, it is referred to the boundary conditions of the region of interest that is the frontiers delimiting the region of interest.

In the second regularization term, the minimization of the gradient of the solution is weighted by a function preserving the edges and therefore imposes smoothness constraints of the magnitude images.

Error is accounted by adding a weight based on the signal to noise ratio of the images in the minimization term.

Consequently, the matrix problem is solved by minimizing the following expression:

$$\min_{\hat{\chi}}(\|W_0 \cdot (C\hat{\chi} - B_{int})\|_2^2 + \alpha^2 \cdot \|M\hat{\chi}\|_2^2 + \beta^2 \cdot \|W_1 \nabla \hat{\chi}\|_2^2)$$

The first term $\|W_0 \cdot (C\hat{\chi} - B_{int})\|_2^2$ is a term that is devoted to ensure fidelity to the data of the provided images in the least-square sense.

$W_0$ the matrix weighting the error in the image based on the signal-to-noise ratio (SNR). Given that the noise standard deviation in the internal field map is inversely proportional to the SNR of the magnitude images, the root-sum-of-squares of the magnitude images is used as a surrogate for the SNR normalization so that the $W_0$ maximum value was equal to one:

$$w_0 = \frac{\sqrt{\sum_{i=1}^{6} Imag_i^2} - \max\left(\sqrt{\sum_{i=1}^{6} Imag_i^2}\right)}{\max\left(\sqrt{\sum_{i=1}^{6} Imag_i^2}\right)}$$

where $Imag_i$ is the magnitude image of the $i^{th}$ echo.

The second term $\alpha^2 \cdot \|M\hat{\chi}\|_2^2$ is similar to imposing a Dirichlet-like boundary conditions.

M is a diagonal matrix which represents the boundary conditions with ones outside the volume of interest and zeros inside the volume of interest.

Such matrix is called an invert mask.

The relative influence of this second term is controlled by a first parameter $\alpha$.

The third term $\beta^2 \cdot \|W_1 \nabla \hat{\chi}\|_2^2$ is similar to imposing a Neumann-like boundary conditions.

$\nabla$ denotes the gradient operator in the three directions and the matrix $W_1$ is a diagonal matrix describing smoothness constraints on the susceptibility distribution.

For instance, the matrix $W_1$ is chosen as the inverse of the magnitude image gradient.

The relative influence of this second term is controlled by a second parameter $\beta$.

Both parameters $\alpha$ and $\beta$ are thus scalars controlling the relative strength of the regularization terms.

For example, the ratio of the first parameter $\alpha$ to the second parameter $\beta$ is comprised between 1 and 3, preferably between 1.5 and 2.5.

In the remainder of the specification, the first parameter $\alpha$ is equal to 15 and the second parameter $\beta$ is equal to 5.

To avoid forming explicitly the matrices C and $\nabla$, C is construed as a pointwise multiplication in the frequency domain and the gradient operator $\nabla$ is conducted by $[-1,1]$ convolution in the spatial domain.

In such case, the previous equation is converted in minimizing $A \cdot \chi - B$ with:

$$A = C^T W_0^T W_0 C + \alpha^2 M^T M + \beta^2 \nabla^T W_1^T W_1 \nabla$$

$$B = C^T W_0^T W_0 C \cdot B_{int}$$

where $^T$ is the Hermitian transpose of matrix.

The solution of this minimization problem was computed iteratively using conjugate gradients with a high number of iterations.

By "high number", it is meant at least 100 iterations by less than 1000 iterations.

At this end of the step of reconstructing S40, the map of FIG. 19 is obtained.

Advantages of the Proposed Method

The proposed method enables to obtain the desired data in a single MR acquisition. The method is therefore less invasive.

Moreover, the proposed method is the first to enable to simultaneously quantify hepatic fat content, fatty acid composition, transverse relaxation time and magnetic susceptibility from a single breathhold MR acquisition.

In other words, the method shows that the determination of internal magnetic susceptibility is feasible in the liver and that its implementation can be done in an imaging sequence providing quantification of fat percentage and fatty acid composition.

Such method is notably applicable to patients with non-alcoholic fatty liver disease.

Such method relies on a combination of techniques, among which a model-based fat-water separation and FA composition quantification, projection onto dipole technique and single orientation Bayesian regularization in k-space including spatial priors iteratively solved by conjugate gradients.

The experiments carried out by the Applicant (see experimental section) shows that such method is relevant and provides a reduced computing time compatible with an in-vivo observation.

It is to be noted that some of the techniques used in the method for post-processing are transposed from other region of interest, notably the brain.

However, the transposition is difficult for various reasons.

The images are to be compatible with apnea for the liver which is not problematic for the brain.

In addition, the transversal relaxation time for the liver is shorter that for the brain which requires a specific acquisition of the images.

Another difficulty is the presence of fat in the liver in pathological cases which results in further inhomogeneity in the magnetic field. This difficulty is circumvent by the fact that the phase correction step included in the fat-water separation and fatty acid composition quantification pipeline is useful for the magnetic quantification since it provide with a $B_0$ inhomogeneity map independent of fat effects.

The fact that the abdominal cavity has multiple air-tissue interfaces and lipid-tissue interface also raises issues of high local gradient in the susceptibility (this results in complexifying the internal and external field separation).

Moreover, the fact that abdomen is a voluminous and inhomogeneous organ has to be considered.

The method for post-processing may be used advantageously in other methods, the adaptation to these methods being immediate.

Notably, the method for post-processing may also be adapted for a method for diagnosing an obesity related disease, a method for identifying a therapeutic target for preventing and/or treating an obesity related disease, a method for identifying a biomarker, the biomarker being a diagnostic biomarker of an obesity related disease, a prognostic biomarker of an obesity related disease or a predictive biomarker in response to the treatment of an obesity related disease and a method for screening a compound useful as a probiotic, a prebiotic or a medicine, the compound having an effect on a known therapeutical target, for preventing and/or treating an obesity related disease.

The embodiments and alternative embodiments considered here-above can be combined to generate further embodiments of the invention.

EXPERIMENTAL SECTION

Experiments were carried out by an Applicant and are illustrated by the FIGS. 20 to 28. These experiments are detailed below.

One aim of this study was to develop a multiparametric approach to combine the quantification of fat content, fatty acid composition, transverse relaxation time and magnetic susceptibility with a single MR acquisition. The feasibility of differentiating between patients with simple steatosis and non-alcoholic steatohepatitis (NASH) was assessed.

Material and Methods

Patients

Magnetic resonance imaging was performed in 31 consecutive patients with biopsy proven NAFLD. Maximum delay between magnetic resonance imaging and biopsy was two months. Eleven patients (5 women, 6 men) had simple steatosis and 20 patients (3 women, 17 men) had NASH.

MR Acquisition

Acquisitions were performed on a Philips Ingenia 3.0 T system (Philips, Best, The Netherlands) with 40 mT·m$^{-1}$ gradient amplitude. A 3D spoiled-gradient multiple echo sequence (3D $T_1$ FFE) with parallel imaging and sensitivity encoding (SENSE) was used, as well as a 32-channel phase array body coil and multi transmit parallel radiofrequency transmission technology. Acquisition parameters were:

TR/flip angle equal to 10 ms/3°;
SENSE factors, 1.5 and 1.8 according to slice and phase direction respectively;
2000 Hz·pixel$^{-1}$ receiver bandwidth and
2 signal averages.

Geometric parameters were:

field of view, 420×380×160 mm3;
acquisition matrix, 140×128×20 ((256×256×40) after interpolation).

Twenty slices of 8 mm thickness (40 of 4 mm after interpolation) in the transverse plane were acquired using eight echoes: n×1.15 ms with n=1, . . . , 8. Total scan duration was 20 s. Phase and magnitude images were saved systematically.

Images Reconstruction

The reconstruction process was implemented using Matlab (The MathWorks Inc., Natick, Mass., USA) and corresponds to carrying out the method as previously described.

Statistical Analysis

For all subject, the liver was manually segmented by the user from the magnitude native images and the mask was applied on each parametric map to derived the mean fat fraction, transversal relaxation time, magnetic susceptibility, saturated, monounsaturated and polyunsaturated fractions values.

The statistical significance of each MR imaging parameter in discriminating simple steatosis and NASH was evaluated with the non parametric Mann-Whitney test. To assess the diagnostic value of the method to discriminate between NASH and simple steatosis, receiver operating characteristic (ROC) analysis was performed. Correlations were assessed with non-parametric Spearman coefficients. P-values<0.05 were considered to be statistically significant.

Results

The results can be found in Table 1 and on FIGS. 20 to 28. Table 1 is reproduced below.

TABLE 1

Quantitative MR imaging parameters in patients with simple steatosis and NASH

|  | Simple steatosis | NASH | p-value |
| --- | --- | --- | --- |
| Fat fraction (%) | 10 ± 6.3 | 11.4 ± 6.5 | 0.20 |
| $T_2$* (ms) | 19.5 ± 4.1 | 19.6 ± 4.5 | 0.32 |
| Susceptibility (ppm) | 0.1 ± 0.08 | −0.30 ± 0.30 | <0.001 |
| Saturated fatty acids (%) | 43.8 ± 4.8 | 50.5 ± 5.7 | <0.05 |
| Monounsaturated fatty acids (%) | 36.8 ± 1.5 | 35.0 ± 2.2 | 0.16 |
| Polyunsaturated fatty acids (%) | 19.4 ± 3.4 | 14.6 ± 3.8 | 0.10 |

Between simple steatosis and NASH, liver fat fraction and $T_2$* were similar (fat fraction: 10.0±6.3% and 11.4±6.5%; transverse relaxation time: 19.5±4.1 ms and 19.6±4.5 ms in simple steatosis and NASH groups respectively). Due to a lack of sensitivity, fatty acid composition quantification cannot be done in patients with low liver fat content (i.e. PDFF<15%). The threshold of 15% corresponds approximatively at the PDFF value separating between histological grade 1 and grade 2 of liver steatosis.

Finally, fatty acid composition was quantified in 5 patients with simple steatosis and 5 patients with NASH. Nevertheless, despite the small number of measurements in the two groups, differences in fatty acid composition were observed. Saturated fatty acid fraction was significantly lower in simple steatosis than in NASH (43.8±4.8% versus 50.5±5.7%; p<0.05), whereas polyunsaturated fatty acid fraction tended to increase (19.4±3.4% versus 14.5±3.8%; p=0.1). Mono unsaturated fatty acid fractions were similar in the two groups (36.8±1.5 and 35.0±2.2%; p=0.16 in the simple steatosis and NASH groups respectively).

Significant decrease of magnetic susceptibility was observed in NASH patients relative to patients with simple steatosis (−0.30±0.30 ppm versus 0.10±0.08 ppm; p<0.001).

Such decrease appears when contemplating the FIGS. 20 to 25. There figures are boxplots of quantitative MR parameters in patients with simple steatosis and NASH. Whereas no significant variations of fat fraction or $T_2$* are observed between simple steatosis and NASH, magnetic susceptibility significantly decreases in NASH and saturated fatty acid fraction significantly increases. Lines within boxes represent median; lower and upper limits of boxes represent 25th and 75th percentiles and whiskers represent 10th and 90th percentiles.

The potential relationships between liver fat content and magnetic susceptibility or $T_2^*$ were also analyzed. No correlation was found between fat fraction and magnetic susceptibility (p=0.04, [95% CI: −0.33-0.39], p=0.84) as well as between fat fraction and $T_2^*$ (p=−0.15, [95% CI: −0.48-0.23], p=0.43).

Figure 26:
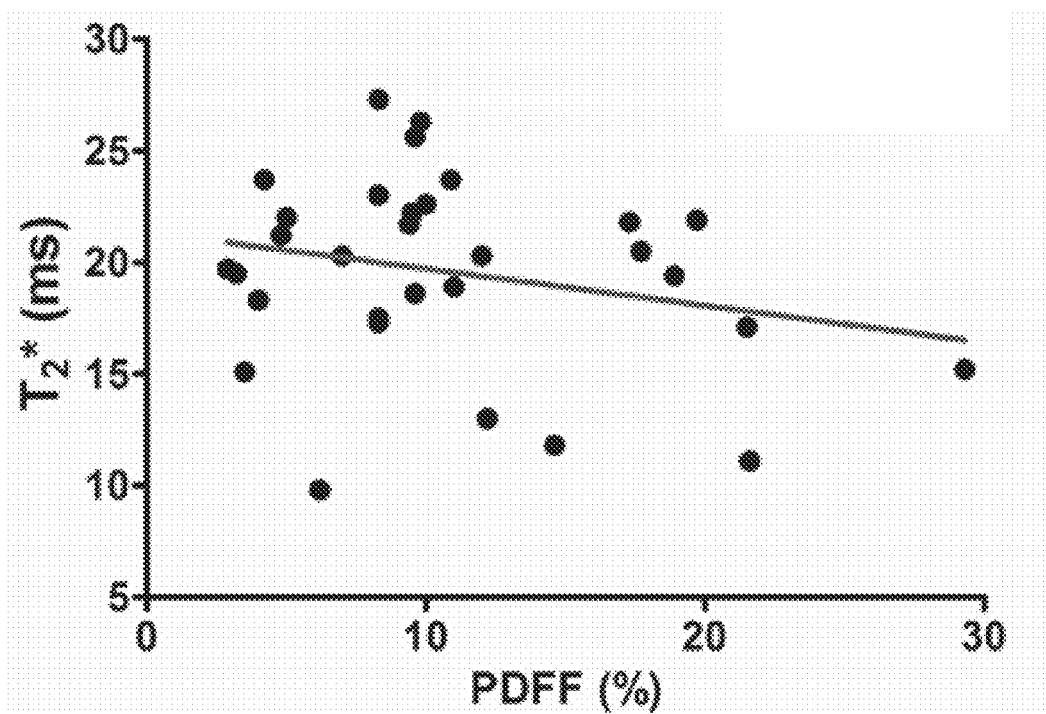
Figure 27:
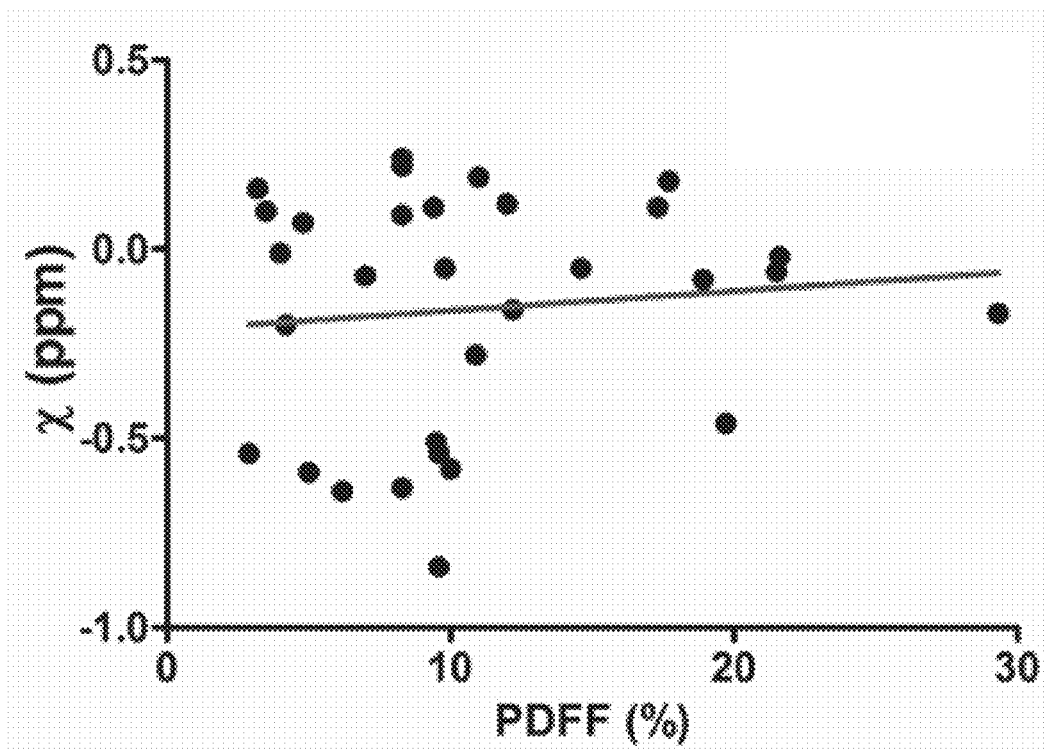
Figure 28:
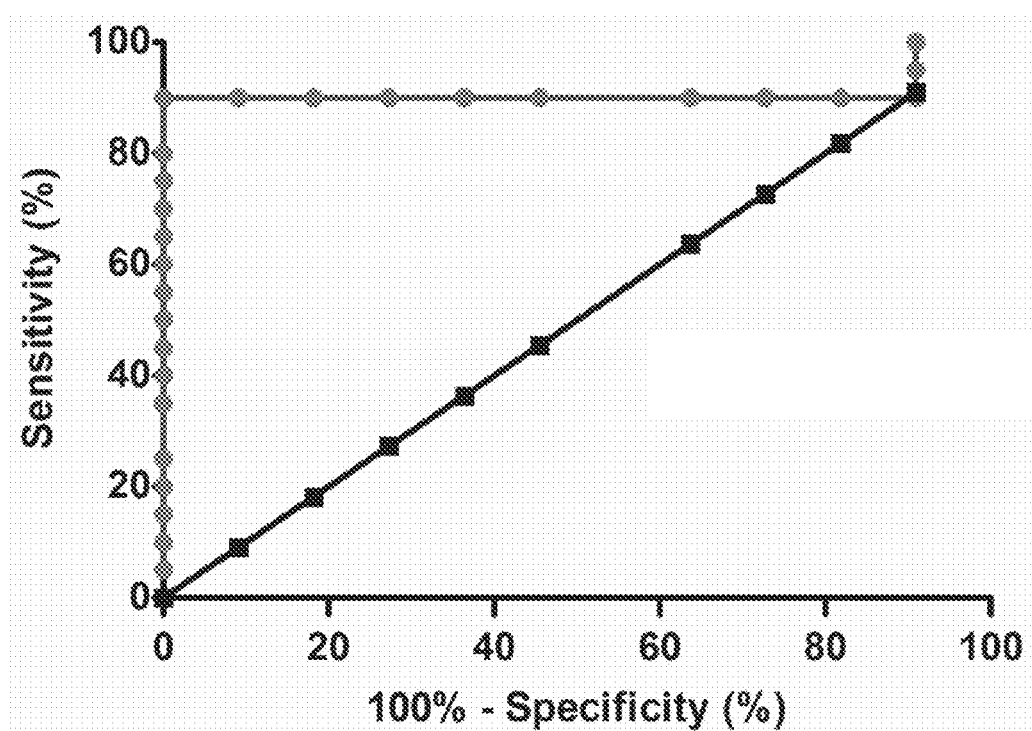

This is notably illustrated by FIGS. 26 and 27 which show the correlation between liver PDFF and liver T2* or magnetic susceptibility. Any correlation was found between liver $T_2^*$ and PDFF well as between liver magnetic susceptibility and PDFF suggesting that liver magnetic susceptibility changes are not linked to the fat content and $T_2^*$ measurement was not dependent on the fat content.

Areas under the ROC curves of magnetic susceptibility to distinguish between simple steatosis and NASH were: 0.91 (95% CI: 0.79-1.03). No correlation was found between hepatic fat fraction and magnetic susceptibility (r=0.04, [95% CI: −0.33-0.39], p=0.84).

AUROC [Please let us know the meaning of AUROC] for magnetic susceptibility as NASH marker was 0.91 (95% CI: 0.79-1.03). This is notably visible in FIG. 28 which shows the receiver operating characteristic curve to assess the performance of magnetic susceptibility in the diagnosis of NASH.

Discussion

To the best of our knowledge, we are the first to report a method to simultaneously quantify hepatic fat content, fatty acid composition, transverse relaxation time and magnetic susceptibility from a single, breathhold MR acquisition. Our results show that QSI is feasible in the liver and that its implementation can be done in an imaging sequence providing quantification of fat percentage and fatty acid composition. The short echo spacing that is needed for accurate fat-water separation is useful for the QSI reconstruction because wraps between echoes are reduced. The drawback of the method is that the phase-to-noise ratio is not optimal because the echo train length is shorter than $T_2^*$. Nevertheless, this effect is limited by the high number of echoes and because liver $T_2^*$ is short.

As observed in our study, magnetic susceptibility is relevant to distinguish between simple steatosis and NASH. As previously reported, the decreased susceptibility observed in NASH may be related to the high diamagnetic protein content caused by inflammation and fibrosis (34, 38, 39). In contrast, magnetic susceptibility changes between simple steatosis and NASH cannot be related to the liver fat content because liver fat fraction was similar in simple steatosis and NASH and no correlation was found between liver fat fraction and magnetic susceptibility.

Regarding fatty acid composition, changes have been observed between NASH and simple steatosis, with an increase of saturated to polyunsaturated fatty acids balance. These results are in agreement with previous reported result according to which a depletion of n-3 and n-6 polyunsaturated fatty acids in NASH in comparison to simple steatosis.

In conclusion, simultaneous quantification of fat content, fatty acid composition, $T_2^*$ and magnetic susceptibility is feasible in the liver and can provide relevant multiparametric information in patients with non-alcoholic fatty liver disease.

LIST OF ABBREVIATIONS

In the description, the following abbreviations are used:
CL: Chain Length
FA: Fatty Acid
FF: Fat Fraction
MR imaging: Magnetic Resonance imaging
MUFA: MonoUnsaturated Fatty Acid
NAFLD: Non Alcoholic Fatty Liver Disease
NASH: Non Alcoholic Steato-Hepatitis
NDB: Number of Double Bonds
NMIDB: Number of Methylene-Interrupted Double Bonds
PDFF: Proton Density Fat Fraction
PUFA: PolyUnsaturated Fatty Acid
ROC: Receiver Operating Characteristic
ROI: Region of Interest
SAT: Subcutaneous Adipose Tissue
SFA: Saturated Fatty Acid
SNR: Signal to Noise Ratio
VAT: Visceral Adipose Tissue

The invention claimed is:

1. A method for post-processing images of a region of interest (ROI) of the liver of a subject to obtain determined parameters, the images being acquired with a magnetic resonance imaging technique, the magnetic resonance imaging technique involving successive echoes of a multiple-gradient echo sequence, each image associating to each pixel of the image the amplitude of the measured signal in the magnetic resonance imaging technique and the phase of the measured signal in the magnetic resonance imaging technique, the method for post-processing comprising at least the step of:
   obtaining in each image the heterogeneous magnetic field, the heterogeneous magnetic field being the sum of an internal magnetic field and an external magnetic field, by:
   unwrapping the phase of each image, to obtain unwrapped images,
   extracting the first-order phase from the unwrapped images,
   calculating the heterogeneous magnetic field based on the extracted first-order phase,
   separating the internal magnetic field from the external magnetic field in the heterogeneous magnetic field by:
   calculating the external magnetic field by decomposing the heterogeneous magnetic field into a field generated by dipoles outside the region of interest (ROI); and
   subtracting the calculated external magnetic field from the heterogeneous magnetic field using a projection onto dipole field method, to obtain the internal magnetic field,
   reconstructing a map of the internal magnetic susceptibility based on the internal magnetic field by using a Bayesian regularization approach to inverse the internal magnetic field, the reconstructed map being a determined parameter, and
   displaying the reconstructed map.

2. A method for post-processing images according to claim 1, wherein said decomposing of the heterogeneous magnetic field comprises using a projection in Hilbert space and minimizing a distance between the field generated by dipoles outside the region of interest and the heterogeneous magnetic field.

3. A method for post-processing images according to claim 2, wherein the distance is pondered by a normal distribution.

4. A method for post-processing images according to claim 1, wherein the Bayesian regularization approach comprises a first regularization term taking into account the signal to noise ratio of each images.

5. A method for post-processing images according to claim 1, wherein the Bayesian regularization approach comprises a second regularization term taking into account the boundary conditions of the region of interest.

6. A method for post-processing images according to claim 1, wherein the Bayesian regularization approach comprises a third regularization term depending from the inverse of the amplitude image gradient.

7. A method for post-processing images according to claim 1, wherein the steps of separating and reconstructing both implies a minimization, the minimization being carried out by using a conjugate gradient technique.

8. A method for post-processing images according to claim 1, wherein the method for post-processing further comprises the step of determining fat characterization parameters, the fat characterization parameters being determined parameters and the step of determining comprises:
   extracting a real signal over echo time for at least one pixel of the unwrapped images, to obtain at least one extracted real signal,
   calculating fat characterization parameters by using a fitting technique applied on a model,
   the model being a function which associates to a plurality of parameters each extracted real signal, the plurality of parameters comprising at least two fat characterization parameters and at least one parameter obtained by a measurement,
   the fitting technique being a non-linear least-square fitting technique using pseudo-random initial conditions.

9. A method for predicting that a subject is at risk of suffering from an obesity related disease, the method for predicting at least comprising the step of:
   carrying out the steps of a method for post-processing images of the subject, to obtain determined parameters, the method for post-processing images being according to claim 1,
   predicting that the subject is at risk of suffering from the obesity related disease based on the determined parameters.

10. A method for diagnosing an obesity related disease, the method for diagnosing at least comprising the step of:
   carrying out the steps of a method for post-processing images of the subject, to obtain determined parameters, the method for post-processing images being according to claim 1, and
   diagnosing the obesity related disease based on the determined parameters.

11. A method for identifying a therapeutic target for preventing or treating an obesity related disease, the method comprising the steps of:
   carrying out the steps of a method for post-processing images of a first subject, to obtain first determined parameters, the method for post-processing images being according to claim 1 and the first subject being a subject suffering from the obesity related disease,
   carrying out the steps of the method for post-processing images of a second subject, to obtain second determined parameters, the method for post-processing images being according to claim 1 and the second subject being a subject not suffering from the obesity related disease,
   selecting a therapeutic target based on the comparison of the first and second determined parameters.

12. A method for identifying a biomarker, the biomarker being a diagnostic biomarker of an obesity related disease, a prognostic biomarker of an obesity related disease or a predictive biomarker in response to the treatment of an obesity related disease, the method comprising the steps of:
   carrying out the steps of a method for post-processing images of a first subject, to obtain first determined parameters, the method for post-processing images being according to claim 1 and the first subject being a subject suffering from the obesity related disease,
   carrying out the steps of the method for post-processing images of a second subject, to obtain second determined parameters, the method for post-processing images being according to claim 1 and the second subject being a subject not suffering from the obesity related disease,
   selecting a biomarker based on the comparison of the first and second determined parameters.

13. A non-transitory computer-readable medium on which is stored a computer program product comprising instructions for carrying out the steps of a method according to claim 1 when said computer program product is executed on a computer device.

14. A device for analyzing a region of interest of the liver of a subject, the device comprising a processor adapted to carry out a method according to claim 1.

* * * * *